United States Patent
Skakoon et al.

[11] Patent Number: 5,321,392
[45] Date of Patent: Jun. 14, 1994

[54] INFUSION PUMP WITH BATTERY BACK-UP

[75] Inventors: James G. Skakoon, Melrose, Mass.; Paul Tamura, Seattle, Wash.

[73] Assignee: Baxter International Inc., Deerfield, Ill.

[21] Appl. No.: 778,557

[22] Filed: Oct. 18, 1991

[51] Int. Cl.[5] .......................................... G08B 21/00
[52] U.S. Cl. .................................. 340/636; 340/635; 429/92; 320/48
[58] Field of Search ................. 340/636, 635, 825.44; 429/90.91, 90.92; 320/48, 2; 128/DIG. 12; 324/427, 434; 604/67, 152

[56] References Cited

U.S. PATENT DOCUMENTS

| | | | |
|---|---|---|---|
| 3,786,343 | 1/1974 | Ehlers | 324/434 |
| 3,985,133 | 10/1976 | Jenkins et al. | 128/DIG. 12 X |
| 4,147,838 | 4/1979 | Leffingwell | 429/1 |
| 4,380,726 | 4/1983 | Sado et al. | 320/48 |
| 4,392,101 | 7/1983 | Saar et al. | 320/20 |
| 4,484,140 | 11/1984 | Dieu | 324/434 |
| 4,489,268 | 12/1984 | Beachy | 320/2 |
| 4,577,144 | 3/1986 | Hodgman et al. | 320/2 |
| 4,593,409 | 6/1986 | Miller | 320/48 X |
| 4,622,508 | 11/1986 | Matteau et al. | 320/48 X |
| 4,645,325 | 2/1987 | Inoue et al. | 354/484 |
| 5,032,825 | 7/1991 | Kuznicki | 340/636 |
| 5,140,310 | 8/1992 | DeLuca et al. | 340/636 |

OTHER PUBLICATIONS

Gates Energy Products, Brochure, Sep. 1987.
Controlled Studies of a New Microprocessor-Based Portable Infusion Pump By: Robert T. Dorr, Sydney E. Salmon, Mary E. Marsh and Aurelia Robertone vol. 3, No. 2, 1986.

Primary Examiner—Jeffery A. Hofsass
Attorney, Agent, or Firm—Kane, Dalsimer, Sullivan, Kurucz, Levy, Eisele & Richard

[57] ABSTRACT

An infusion pump is powered either from an ac line, a disposable battery or a rechargeable battery. The pump automatically differentiates between disposable and rechargeable batteries, and it includes an alarm activated when the pump senses that the battery has been depleted in accordance with the kind of battery in use.

16 Claims, 1 Drawing Sheet

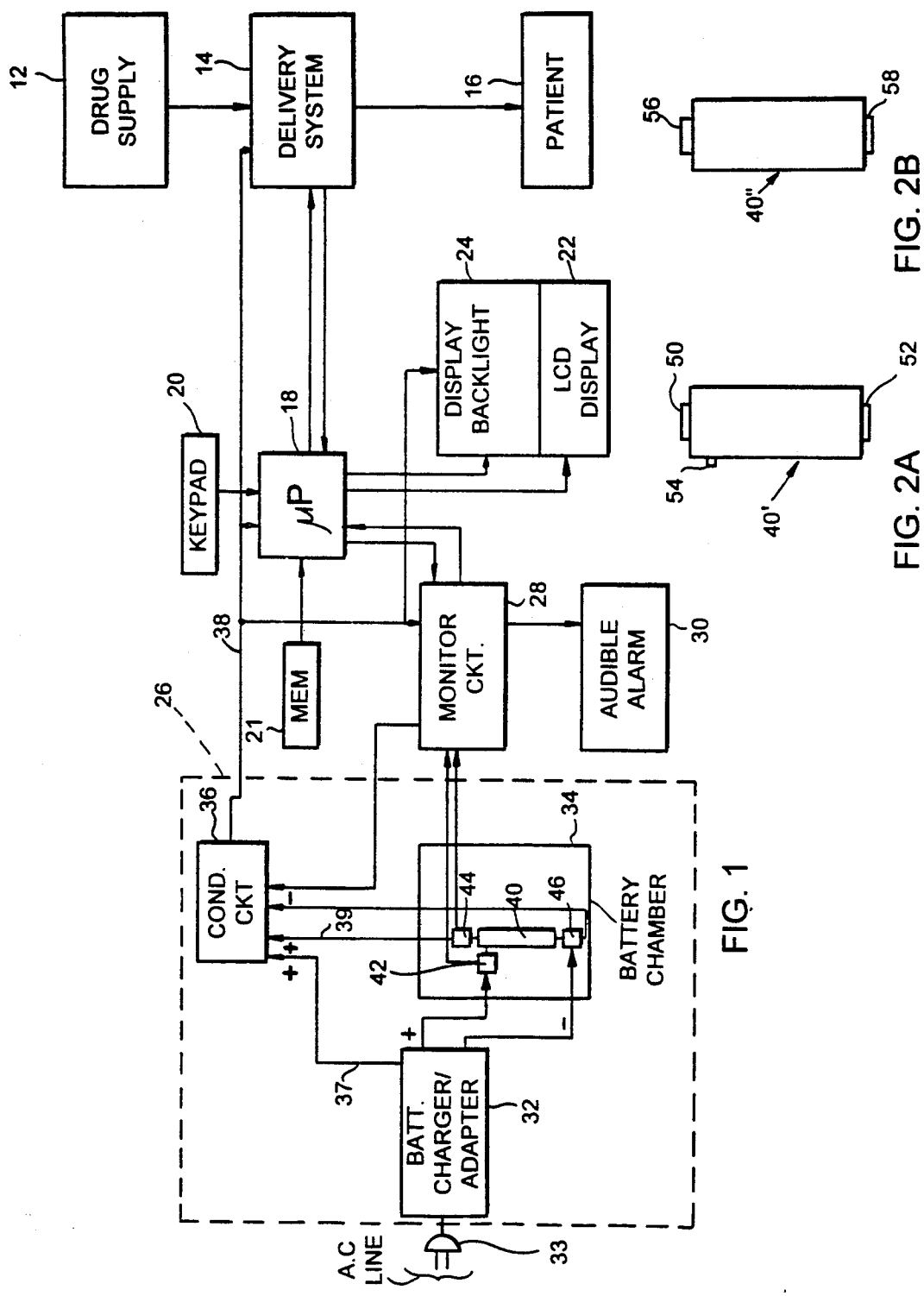

INFUSION PUMP WITH BATTERY BACK-UP

BACKGROUND OF THE INVENTION

1. Field of Invention

This invention pertains to an infusion device such as a patient controlled analgesic pump and the like with dual power supply, and more particularly to a microprocessor-controlled infusion device which can be powered by an AC supply, by rechargeable batteries, or by disposable batteries, and which device determines its supply automatically and adjusts its operation accordingly.

2. Description of the State of the Art

Infusion devices generally use two kinds of power schemes: disposable batteries, or AC power with rechargeable backup batteries. Disposable batteries are best for devices with low power consumption, which are moved frequently from one location to another, or which are not used on a continuous basis. AC systems with rechargeable batteries are best for continuous use or for applications where patient transport is limited. However, sometimes it is desirable to use the same device for both types of applications.

Frequently infusion devices are equipped with a power monitoring circuit which monitors the voltage level of the device power supply and activates an alarm when it senses a low power condition. However, rechargeable batteries and disposable batteries have different discharge characteristics, and therefore if the monitoring circuit is set to sense a voltage level appropriate for one of the batteries, the indication will not be effective for sensing the reserve power of the other type of battery.

OBJECTIVES AND SUMMARY OF THE INVENTION

In view of the above, an objective of the present invention is to provide an infusion device which can be powered from an AC supply, by backup rechargeable batteries, or by disposable batteries.

A further objective is to provide an infusion device which automatically determines its power supply.

A further objective is to provide an infusion device with a power monitoring circuit which enables the infusion device to indicate the correct power reserve of its supply. Other objectives and advantages of the invention shall become apparent from the description of the invention.

An infusion pump system constructed in accordance with this invention includes pump means for delivering a drug to a patient; a power supply for providing power to said pump means, said power supply including battery holder means for accepting at least one battery selected from a group formed of rechargeable batteries and disposable batteries; monitoring means for monitoring said power supply to determine a reserve energy level of said power supply means; and alarm means coupled to said monitoring means for generating an alarm signal when said reserve energy level falls below a threshold.

BRIEF DESCRIPTION OF THE DRAWINGS

FIG. 1 shows a schematic diagram of an infusion device constructed in accordance with this invention;

FIG. 2A shows schematically a rechargeable battery that can be used in the device of FIG. 1; and FIG. 2B shows schematically a disposable battery that can be used with the device of FIG. 1.

DETAILED DESCRIPTION OF THE INVENTION

Referring now to the drawings, an infusion pump system 10 which may be for example a patient controlled analgesia pump, constructed in accordance with this invention includes a drug reservoir 12 coupled to a drug delivery system 14 for delivering a drug to a patient 16. The delivery system is controlled through a microprocessor 18.

The infusion pump system 10 is controlled by a microprocessor 18 and an associated memory 21. This memory 21 holds, among other information, information related to the operating characteristics of both rechargeable and disposable batteries. For example, memory 21 may hold a table relating for each battery the amount of usable energy left in that battery (in amp-hours) as a function of the output voltage of that battery. System status information as well as operation instructions are provided to a user on an LCD display 22. Since this type of display is hard to read under low ambient lighting conditions, display 22 is provided with a backlight 24. User inputs are accomplished through keypad 20. Power to these system components is supplied by a power supply 26. This supply 26 is monitored by a monitoring circuit 28 used to detect the source of primary power for the system. Moreover, if batteries are supplying the primary power, than the monitoring circuit in conjunction with microprocessor 18 and memory 21, is also used to determine the energy reserve of the batteries. If this reserve falls below a threshold, an alarm 30 is activated to indicate that the batteries must be changed or charged. Alarm 30 may also include indicators for various functions, such as, an indicator for a dead battery.

The power supply 26 is coupled to an AC source through a plug 33. The power supply also includes a battery charger/adapter 32, a battery chamber 34 and a power conditioning circuit 36. The output of circuit 36 provides the power to the system components through a bus 38. Battery chamber 34 holds one or more batteries 40. Importantly, the chamber is provided with three ports 42, 44, 46 for battery contact. Ports 44 and 46 are the standard positive and negative ports. Port 42 is used for coupling to a charging terminal (if any) on battery 40.

The system 10 may be used with either rechargeable batteries or disposable batteries. As shown in FIG. 2A, a rechargeable battery 40' is preferably equipped with two standard terminals 50, 52, as well as a charging terminal 54. This type of rechargeable battery is disclosed for example in U.S. Pat. Nos. 4,147,838 and 4,489,268. As disclosed in the patents, in this type of battery terminal 54 is shorted internally to positive post 50. A typical disposable battery 40" shown in FIG. 2B has only two terminals 56, 58.

The system operates as follows. In one configuration, a rechargeable battery such as 40' is inserted into battery chamber 34 with terminals 50, 52 and 54 coupled to ports 44, 46 and 42 respectively. Plug 33 is inserted into a standard AC outlet and battery charger/adapter 32 provides power for charging battery 40' and for operating the infusion pump. For example, as shown in U.S. Pat. No. 4,147,838, the battery charger may include a transformer with its primary coil connected to line voltage and the secondary coil connected to the charging port through a resistor and a diode. Conditioning circuit 36 further conditions the charger adapter 32 output (line 37) or the battery output (line 39) and generates one or more power signals on bus 38 for the system components.

The monitoring circuit 28 monitors the voltage level on ports 42 and 44 and if it senses the charging voltage, it sends a signal to microprocessor 18 that the primary power source is the AC line. The monitor circuit 28 also compares the voltage on port 42 to the voltage on port 44. If they are the same then (since these two ports are shorted internally within battery 40') it is assumed that a rechargeable battery is in place. During normal operation, the microprocessor 18 controls and enables all the system circuitry, including for example the display backlight 24.

The primary source of power for the system is the A.C. line, through line 37 to conditioner 36. If the AC source is disconnected (or fails), primary power to the system is provided by battery 40' without interruption, and the voltage of ports 42 and 44 drop to the output voltage of the battery. Circuit 28 now senses that change in the voltage of these ports 42, 44 and sends a signal to the microprocessor 18 to indicate that the AC line has been disconnected and that the power is provided by the rechargeable battery 40'. The infusion pump then enters into a first battery operation mode. In the first battery operation mode, the microprocessor monitors the voltage of battery 40', and based on the information from memory 21 calculates the minimum energy requirement for the system based on the system power consumption for a preset time period, for example 30 minutes. The microprocessor 18 then determines a threshold voltage level corresponding to said minimum time period. Said voltage level is then used by monitoring circuit 28. The microprocessor also powers down or disables certain non-essential system components which use excessive power such as the display backlight 24. More particularly, during the first battery operation condition, the backlight 24 might never be turned on. Alternatively, it may be turned on for a preselected time period (i.e. 30 seconds) when the keypad 20 is activated.

As long as the system is operated in the first battery operation mode, the circuit 28 continues to monitor the battery voltage on port 44 to sense if the battery has been depleted. If this voltage falls below the threshold voltage level set by the microprocessor 18, the monitoring circuit 28 sends an alarm signal to the microprocessor and the audible alarm 30 is activated.

In the second configuration, disposable battery 40" is inserted into chamber 34, and plug 33 is not connected to the AC line. In this configuration, port 42 is not connected to port 44 through battery 40". Circuit 28 now senses that a disposable battery is used as a primary source and sends a corresponding signal to the microprocessor 18. The microprocessor then enters into and operates in a second battery operation mode, similar to the first battery operation mode except that the threshold voltage for the circuit 28 is calculated by the microprocessor 18 based on information from memory 21 descriptive of disposable batteries.

In an alternate, third configuration, disposable battery 40" is inserted into chamber 34, and plug 33 is connected to the AC line. In this configuration, since port 42 makes no connection to a corresponding battery terminal, disposable battery 40" is not charged by charger/adapter 32. Further, circuit 28 in conjunction with the microprocessor preferentially selects charger/adapter 32 through conditioning circuit 36 as the power source. Nevertheless, upon disconnection or failure of the AC source, circuit 28 senses this condition and chooses the battery 40" as the power source without interruption. The infusion pump then operates as in the second configuration. Reinstatement of the AC line power will result in automatic reselection of the charger/adapter 32 as power source.

In the above description, the monitoring circuit 28 has been treated as a discrete system component for the sake of clarity. However it should be understood that this circuit may be fully or partially integrated into the microprocessor by software implementation.

Numerous other modifications may be made to this invention without departing from its scope as defined in the appended claims.

We claim:

1. An infusion pump system comprising;
   pump means for delivering a drug to a patient;
   a power supply for providing power to said pump means, said power supply including battery holder means and a battery disposed in said battery holder, said battery being one of a disposable and a rechargeable battery, said battery holder including a first and a second contact for contacting the terminals of said disposable battery and an additional contact for contacting an additional terminal of said rechargeable battery;
   monitoring means coupled to said contacts to detect the type of battery connected to said contacts for monitoring said power supply to determine a reserve energy level of said power supply; and
   an alarm means coupled to said monitoring means for generating an alarm signal when said reserve energy level falls below a threshold.

2. The pump of claim 1 wherein said power supply includes connecting means for connecting to an ac line.

3. The pump of claim 1 wherein said monitoring means includes differentiating means for differentiating between said rechargeable battery and said disposable battery, said monitoring means setting said threshold to a level dependent on the type of battery determined.

4. The pump of claim 1 further comprising a microprocessor means for controlling said pump means, said monitoring means being integrated with said microprocessor means.

5. The pump of claim 1 further comprising non-essential circuitry and disabling means for selectively disabling said non-essential circuitry when said power supply uses one type of battery as a primary power source.

6. The pump of claim 1 wherein said alarm means comprises several alarm indication means including a dead battery indication.

7. An infusion pump system comprising;
   pump means for delivering a drug to a patient;
   control means for controlling said pump means;
   a power supply for providing power to said pump means and said control means from a power source selected from the group consisting of an ac line, a rechargeable battery and a disposable battery; said power supply including battery holder means for accepting at least one battery, said battery holder including a first and a second contact for contacting the terminals of said disposable battery and an additional contact for contacting an additional terminal of said rechargeable battery;

monitoring means coupled to said contacts to detect the type of battery connected to said contacts for monitoring a reserve energy level of said power supply; and alarm means activated by said monitoring means for generating an alarm when said reserve energy level is below a threshold.

8. The pump of claim 7 monitoring means for monitoring said power supply, wherein said monitoring means is adapted to differentiate between said rechargeable battery and said disposable battery.

9. The pump of claim 7 further comprising memory means for holding information related to the reserve power characteristics of said rechargeable and disposable battery.

10. The pump of claim 7 further comprising non-essential circuitry, said control means being adapted to selectively disable said non-essential circuitry when one of said rechargeable battery and said disposable battery are the primary source.

11. The pump of claim 8 wherein said monitoring means differentiates between said disposable and rechargeable battery by comparing a voltage between said additional contact and one of said first and second contacts.

12. The pump of claim 7 wherein said power supply further includes a battery charger connected to said ac line, and wherein said monitoring means monitors a voltage on one of said contacts to determine if power is obtained from said ac line, a rechargeable battery or a disposable battery.

13. An infusion pump system comprising;
 (A) pump means for delivering a drug to a patient;
 (B) a power source for said pump means, said power source including
  (1) a battery holder for holding one of a disposable battery having two battery terminals and a rechargeable battery having three battery terminals, said battery holder having a contact for contacting each of said terminals; and
  (2) a battery charger connected to an ac line; and
 (C) monitoring means coupled to said contacts for monitoring a power level of said power source, said monitoring means being adapted to differentiate between said disposable and rechargeable battery by comparing a voltage between said contacts.

14. The pump of claim 13 further comprising alarm means coupled to said monitoring means for generating an alarm when said power level is below a threshold.

15. The pump of claim 14 wherein said threshold is selected based on whether a rechargeable or disposable battery is used.

16. The pump of claim 13 wherein said monitoring means detects when said battery charger is connected to said ac line based on said voltage.

* * * * *